(12) United States Patent
Perovitch et al.

(10) Patent No.: US 8,722,744 B2
(45) Date of Patent: May 13, 2014

(54) GALENICAL FORM FOR THE ADMINISTRATION OF PARACETAMOL BY TRANSMUCOUS MEANS

(76) Inventors: Philippe Perovitch, Le Temple (FR); Marc Maury, Saint Medard en Jalles (FR)

( * ) Notice: Subject to any disclaimer, the term of this patent is extended or adjusted under 35 U.S.C. 154(b) by 786 days.

(21) Appl. No.: 12/520,723

(22) PCT Filed: Dec. 19, 2007

(86) PCT No.: PCT/FR2007/052555
§ 371 (c)(1), (2), (4) Date: Jun. 22, 2009

(87) PCT Pub. No.: WO2008/087323
PCT Pub. Date: Jul. 24, 2008

(65) Prior Publication Data
US 2010/0093710 A1    Apr. 15, 2010

(30) Foreign Application Priority Data
Dec. 21, 2006    (FR) ...................................... 06 55773

(51) Int. Cl.
*A61K 31/16*    (2006.01)

(52) U.S. Cl.
USPC .......................................... 514/630; 514/629

(58) Field of Classification Search
None
See application file for complete search history.

(56) References Cited

U.S. PATENT DOCUMENTS

| 5,981,591 | A | 11/1999 | Deihl |
| 6,127,425 | A * | 10/2000 | Tully ............................. 514/648 |
| 6,767,925 | B1 | 7/2004 | Deihl |

FOREIGN PATENT DOCUMENTS

| WO | 95/23591 | 9/1995 |
| WO | 00/41692 | 7/2000 |

OTHER PUBLICATIONS

Vicks® 44® monograph, Physician's Desk Reference, 2005, pp. 2793-2794.*
International Search Report dated Aug. 4, 2008, from corresponding PCT application.

* cited by examiner

*Primary Examiner* — Sreeni Padmanabhan
*Assistant Examiner* — Jody Karol
(74) *Attorney, Agent, or Firm* — Young & Thompson

(57) ABSTRACT

A galenical form for the transmucous administration of at least one active ingredient, characterized in that the active ingredient is paracetamol in a stable and complete dissolved state in a hydroalcoholic solution that includes at least 10% by mass of alcohol so as to allow fast absorption of the active ingredient through the mucous membranes of the buccal cavity and/or the oropharynx. A process for production and the uses of the galenical form are also disclosed.

2 Claims, No Drawings

GALENICAL FORM FOR THE ADMINISTRATION OF PARACETAMOL BY TRANSMUCOUS MEANS

This invention relates to a galenical form for the instantaneous systemic administration by transmucous means of primarily paracetamol-based analgesic-antipyretic medications.

The invention also relates to a process for production and to uses of the galenical form.

Paracetamol is a very small molecule that is lipophilic in nature and that has an exclusively analgesic and antipyretic, essentially central, pharmacological activity at the level of the passageways and cerebral receptors that regulate pain and fever. Very commonly used to treat fever conditions and medium-intensity pains such as headaches, dysmenorrheas, etc., it is generally administered orally, by itself or in combination with other therapeutic active ingredients, at unit dosages of 500 mg or 1 g.

Such an administration is not satisfactory, however.

Actually, when the paracetamol molecules are introduced into the alimentary canal and the stomach, they undergo the so-called first digestive pass effect, alterations and losses related to the stomach environment or to variations of intestinal physiologies. They are then subjected to a so-called "first hepatic pass" effect, which produces their metabolization and/or their more or less intense degradation, with composition of numerous metabolites, for the most part inactive or toxic, without taking into account that paracetamol is toxic to the liver when it is administered at a dosage that is higher than 4 g.

The dose of truly bioavailable active ingredient is therefore small, evaluated on average between 60 and 75% of the administered dose, without presuming numerous inter- and intra-individual variabilities.

In addition, the half-life of paracetamol is relatively short, between 1 and 3 hours. Very slightly linked to plasmatic proteins because of its lipophilic nature, the paracetamol molecule is very broadly distributed in most of the compartments of the organism. Thus, a major part of the administered dose will find itself diluted in the vascular network of the organism at the same time as it is dispersed in the extra-vascular, organic, and primarily tissue spaces, reducing the actually available portion of paracetamol that is able to gain access to the cerebral central receptors to exert its pharmacological activity there, with a short duration of action.

In addition, the beginning of the therapeutic effectiveness for the patient takes place between 30 and 60 minutes after intake, corresponding to the period of digestive absorption, metabolization, and vascular and then tissue diffusion.

Actually, two major problems appear.

The first problem is that it is necessary to administer an adequate dose to the patient, taking into consideration the dilution and the dispersion in the organism, so that the significantly active part that reaches the central effectors is effective.

The second is the latency period due to the metabolization and the diffusion in the organism before the molecule acts and the patient feels its benefits.

There is therefore a need for a galenical formulation that makes it possible to administer an immediately bioavailable quantity of paracetamol, by itself or in combination with other active ingredients, so as to be able to exert—very quickly and effectively—a therapeutic activity that is in particular analgesic and antipyretic.

This is the purpose of this invention in proposing a galenical form for the administration by transmucous means of at least one active ingredient, characterized in that said active ingredient is paracetamol in a stable and complete dissolved state in a hydroalcoholic solution that comprises at least 10% by mass of alcohol so as to allow fast absorption of said active ingredient through the mucous membranes of the buccal cavity and/or the oropharynx.

The invention is now described in detail.

Transmucous means is defined as any passive passing through the lingual, sublingual, gingival, palatine, or jugal mucous membranes or any other mucous membranes that constitute the buccal cavity and the oropharynx.

The stable and complete dissolved state is defined as a dissolved state that restores the active ingredient to the molecular and weakly ionized state in its dissolved medium, dissolved state that precludes any possibility of an inopportune recrystallization.

Preferably, the galenical form according to the invention comes in the form of a hydroalcoholic solution that comprises between 10 and 70% by mass of alcohol and a water content of between 30 and 90%. The passage in the central systemic circulation of the paracetamol molecules that are formulated according to the invention is therefore carried out in hydroalcoholic solution with a variable degree of alcohol, preferably between 10° and 70°, even more preferably between 25° and 55°.

According to a major characteristic of the invention, the alcohol, present at at least 10% by mass, does not play only the role of solvent, but also that of promoter of an accelerated permucosal absorption, whose speed increases based on the rise of the degree of alcohol that is used.

According to a preferred embodiment of the invention, the hydroalcoholic solution is produced based on water and ethanol.

The coefficient for dissolution of paracetamol in ethanol makes it possible to obtain a complete dissolution of said active ingredient at a level of 250 mg of paracetamol per 2 ml of ethanol at 45%. This coefficient can be modulated based on the degree of alcohol and the water/ethanol ratio that is used. By way of example, a 45% water/ethanol mixture at 50/50 by volume produces a better solubilization of paracetamol, compared to that obtained in pure ethanol.

According to another embodiment, the hydroalcoholic solution can be produced with a base of water and isopropyl alcohol.

The hydroalcoholic solution according to the invention can also comprise one or more adjuvants for dissolution of the active ingredient(s), such as a polymer of the PEG (polyethylene glycol) type with low molecular weight, isopropyl alcohol, a surfactant such as Cremophor, or a polysorbate, and/or alcohol-oil mixtures. It can also contain an aroma or a sweetener for sweetening the taste sensation.

According to a particular embodiment, the galenical form according to the invention can also comprise a pH-correcting agent.

Preferably, the pH-correcting agent is selected from among sodium carbonates and sodium bicarbonates, monosodium or disodium phosphates, triethanolamine, soda (NaOH) and potash (KOH).

The galenical form according to the invention allows paracetamol molecules and optional other active ingredients to passively pass through the mucous membranes of the oropharynx in a length of time that is less than 10 seconds after administration.

This very fast absorption period makes it possible to prevent any stagnation of the solution and of paracetamol in the buccal atmosphere as well as its inopportune mixing with saliva that can alter it, which would introduce a break in the continuity and the stability of the dissolution of the active ingredient. This short length of time also makes it possible to prevent any reflex swallowing of the solution and of the paracetamol that it contains.

The transmucous passage of paracetamol that is shown in the dissolved state according to the invention from the side of the external epithelial membrane, consisting of phospho-lipidic structures that passively absorb the lipophilic molecules by elective affinity, is based on an osmotic demand to the other side of said membrane, in which the concentration of dissolved active ingredient and that of the alcoholic solution being considered participate together. The osmotic demand is all the more enduring and powerful since the degree of alcohol that is used as an absorption promoter is high. In the particular case of paracetamol, according to the invention, a suitable degree of alcohol is between 10° and 70°, preferably between 25° and 55°. This makes it possible to ensure simultaneously obtaining and adjusting of the best coefficient for dissolution and stabilization of paracetamol as well as the promotion of its permucosal passage in a period of about ten seconds. One particularly suitable embodiment corresponds to 1 ml of hydroalcoholic solution at a degree of alcohol of 45° per 125 mg of paracetamol.

The mucous membranes of the mouth and the oropharynx have a very dense, quasi-spongy network of microvessels, so that the molecules, both of alcoholic solvent and dissolved paracetamol, which pass through the epithelial membrane, are instantaneously captured by the blood micro-circulation and carried toward the sublingual veins. This phenomenon is accentuated by the presence of alcohol that causes vasodilatation and an increase in the microvascular flow rate of the mucous membranes.

There is therefore never equilibrium on either side of the membrane: the concentration in the mouth always remains higher until the mechanism is exhausted when there are no more molecules to be absorbed.

Thus, the entirety of the alcohol and the paracetamol and optional other molecules that are found dissolved there according to the invention pass through the mucous membrane.

The use of the galenical form according to the invention makes it possible to administer passively a paracetamol dose that is immediately absorbed as soon as it is deposited and upon contact with the mucous membrane to be distributed instantaneously to the entire organism vascularly, without any delay for its pharmacological action and without undergoing the major preliminary effects of digestive and hepatic passages. The galenical form according to the invention therefore makes possible an immediacy of tissue absorption of paracetamol, and then its distribution into the central circulation of the organism, which no other existing pharmaceutical form allows, even by intravenous means.

For example, with a galenical form according to the invention that is produced from 250 mg of paracetamol that is solubilized in 2 ml of ethyl alcohol at 45% M/V, it is possible to administer—almost instantaneously and passively—a very significant dose of paracetamol, 250 mg, which corresponds to half the dose that is usually agreed upon and administered by oral means.

The hydroalcoholic solution with an alcohol content of at least 10% by mass according to the invention also has the advantage of protecting the pharmaceutical formulation in relation to a microbiological contamination without having to introduce (an) antimicrobial preservation agent(s).

Advantageously, this invention offers a great simplicity of production and a very good galenical stability: the water/alcohol solution ensures the solubilization of paracetamol while eliminating most of the vehicles that are used in the conventional pharmaceutical forms. It therefore makes it possible both to reduce the production costs and to reduce the risks of intolerance and the possible interactions between active ingredient(s) and vehicles.

Notably, the action periods of the galenical form according to the invention are very short, in particular compared to the slowness of absorption of paracetamol-based medications by the digestive tract. The almost-instantaneous pharmacological release makes it possible for a patient to administer to himself a product for an effect that is almost equivalent to the effectiveness of a flash intravenous injection into the circulatory system.

In addition, whereby paracetamol does not encounter any significant obstacle to its assimilation and its instantaneous distribution into the organism, the basic administered dose is small, very close to the useful dose for exerting the required pharmacological activity. This dose depends, of course, on the desired effect. It is preferably between 25 and 250 mg of paracetamol for volumes of hydroalcoholic solution that vary from 0.5 ml to 2.5 ml.

Furthermore, whereby the oropharyngeal mucous membrane has an extremely large total adsorption surface area, scaled down by its nature of folded, villous tissue, the administration of the galenical form according to the invention is free of any risk of ill-timed swallowing or swallowing the wrong way. Actually, it allows an extremely fast permucosal passage that prevents any salivary dissolving or swallowing of the active ingredient that is administered, with the advantage of not destabilizing the mucous membranes, with surfactant derivatives, for example, as is the case of the existing formulations.

Likewise, the effects of alcohol are insignificant. By way of example, 2 to 4 ml of ethanol at 40° C. would only produce a blood alcohol level of less than 0.2 or 0.4 mg per liter of blood, or 12.5 to 25 times below the legal French tolerances of 0.5 g per liter.

A particularly suitable process for the production of the galenical form according to the invention comprises the following stages:

Introducing two thirds of the paracetamol into alcohol while being stirred,
Stirring the preparation, preferably for 10 to 60 minutes, to ensure the dissolution of the first paracetamol fraction,
Introducing the purified water while being stirred,
Stirring the preparation, preferably for 10 to 60 minutes,
Introducing the remaining third of the paracetamol, and
Stirring until all of the paracetamol is completely dissolved.

The alcohol is preferably initially introduced in a stainless steel tank that is equipped with an explosion-proof stifling system.

According to one embodiment, the process also comprises a stage for filtering the preparation.

The galenical form that is obtained is then distributed by fraction in a suitable packaging.

This invention can be used for the instantaneous systemic administration at small and useful doses of paracetamol by itself. Such a formulation can be used for the production of a medication that has an analgesic and antipyretic therapeutic activity in a very short period and at very small doses relative to traditional doses, making possible in particular the treatment of pain, fever conditions, or migraines.

The galenical form according to the invention can also be used for the instantaneous systemic administration at small and useful doses of paracetamol in combination with other active ingredients, for example designed to treat flu-like diseases with rhinopharyngeal congestion. Such formulations can be used for the production of medications that have spontaneous soothing and sedative effects on the pain and the problems of flu-like diseases and colds.

According to one aspect of the invention, the galenical form requires a specific industrial conditioning so as to prevent the degradation of the active ingredient(s) in contact with the air.

One particular embodiment consists in using a preferably small, opaque, flexible plastic or metalloplastic or glass packaging that is filled under nitrogen atmosphere for the protection of the stability of the composition and the impermeability to oxygen and to radiation. This packaging ensures the dissolution and stability over time of paracetamol and optional other active ingredients that are dissolved in hydroalcoholic solution according to the invention.

For the comfort of use by the patient, for an easy transport, it is preferably possible to resort to packages in the form of specific airtight cases. Still more preferably, the galenical form according to the invention is packaged in single-dose packages of 0.5 to 30 ml, able to provide a suitable dose of active ingredient.

Advantageously, this packaging is easy to transport and makes possible an easy use of the galenical form at any moment of the day.

Other characteristics and advantages will emerge from the following non-limiting examples of the invention.

I. EXAMPLES OF PARACETAMOL FORMULATION BY ITSELF ACCORDING TO THE INVENTION

It is possible to cite several examples of paracetamol formulation by itself according to the invention, particularly suitable for the treatment of migraines or fever conditions.

1—Example of the Formulation of 0.5 ml per 25 mg of Paracetamol

| | |
|---|---|
| Paracetamol: | 25.0 mg |
| Distilled Water: | 0.30 ml |
| Ethanol, Absolute Alcohol | 0.20 ml |
| Sweetener | Sufficient quantity |
| Aroma | Sufficient quantity |

2—Example of the Formulation of 0.5 ml per 50 mg of Paracetamol

| | |
|---|---|
| Paracetamol: | 50.0 mg |
| Distilled Water: | 0.30 ml |
| Ethanol, Absolute Alcohol: | 0.20 ml |
| Sweetener | Sufficient Quantity |
| Aroma | Sufficient Quantity |

3—Example of the Formulation of 1 ml per 100 mg of Paracetamol

| | |
|---|---|
| Paracetamol: | 100.0 mg |
| Distilled Water: | 0.60 ml |
| Ethanol, Absolute Alcohol: | 0.40 ml |
| Sweetener | Sufficient Quantity |
| Aroma | Sufficient Quantity |

4—Example of the Formulation of 1 ml per 150 mg of Paracetamol

| | |
|---|---|
| Paracetamol: | 150.0 mg |
| Distilled Water: | 0.45 ml |
| Ethanol, Absolute Alcohol: | 0.55 ml |
| Sweetener | Sufficient Quantity |
| Aroma | Sufficient Quantity |

5—Example of the Formulation of 2 ml per 200 mg of Paracetamol

| | |
|---|---|
| Paracetamol: | 200.0 mg |
| Distilled Water: | 1.20 ml |
| Ethanol, Absolute Alcohol: | 0.80 ml |
| Sweetener | Sufficient Quantity |
| Aroma | Sufficient Quantity |

6—Example of the Formulation of 2 ml per 250 mg of Paracetamol

| | |
|---|---|
| Paracetamol: | 250.0 mg |
| Distilled Water: | 1.1 ml |
| Ethanol, Absolute Alcohol: | 0.90 ml |
| Sweetener | Sufficient Quantity |
| Aroma | Sufficient Quantity |

II. EXAMPLES OF PARACETAMOL FORMULATION IN COMBINATION WITH OTHER THERAPEUTIC ACTIVE INGREDIENTS ACCORDING TO THE INVENTION

The galenical form according to the invention can be used for instantaneous systemic administration at small and useful doses of paracetamol in combination with other therapeutic active ingredients.

In particular, the galenical form according to the invention can contain—in combination with paracetamol—any lipophilic substance that is compatible with paracetamol in alcoholic solution, able to provide an analgesic, decongestant, sedative adjuvant for the airways and sinus, rhino and oropharyngeal passageways.

By way of example, it is possible to cite formulations according to the invention that are combined with paracetamol:

—Pseudoephedrine

Pseudoephedrine is a small molecule with a daytime decongestant action. It can be added to a paracetamol-based formulation according to the invention, at different dosages that range from, for example, 1 to 30 mg of pseudoephedrine.

By way of nonlimiting example, the following formulation can be cited:

| | |
|---|---|
| Paracetamol: | 150.0 mg |
| Pseudoephedrine: | 10.0 mg |
| Distilled Water: | 0.55 ml |
| Ethanol, Absolute Alcohol: | 0.45 ml |
| Aroma | Sufficient Quantity |

—Triprolidine:

Triprolidine can be added to a paracetamol-based formulation according to the invention, at different dosages that range from, for example, 0.10 to 2.5 mg of triprolidine.

By way of nonlimiting example, the following formulation can be cited:

| | |
|---|---|
| Paracetamol: | 100.0 mg |
| Triprolidine: | 0.25 mg |
| Distilled Water: | 0.60 ml |
| Ethanol, Absolute Alcohol: | 0.40 ml |
| Aroma | Sufficient Quantity |

—Promethazine:

Promethazine can be added to a paracetamol-based formulation according to the invention, at different dosages that range from, for example, 0.15 to 25 mg of promethazine.

—Pheniramine:

Pheniramine can be added to a paracetamol-based formulation according to the invention, at different dosages that range from, for example, 0.10 to 25 mg of pheniramine.

—Meclozine:

Meclozine can be added to a paracetamol-based formulation according to the invention, at different dosages that range from, for example, 0.10 to 25 mg of meclozine.

—Diphenhydramine:

Diphenhydramine can be added to a paracetamol-based formulation according to the invention, at different dosages that range from, for example, 2 to 25 mg of diphenhydramine.

—Dimenhydrinate:

Dimenhydrinate can be added to a paracetamol-based formulation according to the invention, at different dosages that range from, for example, 2 to 25 mg of dimenhydrinate.

—Ciproheptadine:

Ciproheptadine can be added to a paracetamol-based formulation according to the invention, at different dosages that range from, for example, 0.10 to 2.0 mg of ciproheptadine.

The galenical form according to the invention can also contain, in combination with paracetamol, other active molecules that are usually used in combination with paracetamol and for which the formulation in hydroalcoholic form is pertinent. By way of example, formulations according to the invention that are combined with paracetamol can be cited:

—Dextropropoxyfene:

Dextropropoxyfene can be added to a paracetamol-based formulation according to the invention, at different dosages that range from, for example, 5.0 to 15.0 mg of dextropropoxyfene.

—Codeine:

Codeine can be added to a paracetamol-based formulation according to the invention, at different dosages that range from, for example, 5.0 to 15.0 mg of codeine.

Of course, the invention obviously is not limited to the examples shown and described above, but on the contrary covers all of the variants.

The invention claimed is:

1. A method of treating pain, fever conditions or migraines, comprising administering by transmucous means to a subject in need thereof an effective amount of a galenical form for administration by transmucous means of one active ingredient, wherein said active ingredient is paracetamol in a stable and complete dissolved state in a hydroalcoholic solution based on water and ethanol so as to allow quick absorption of said active ingredient through the mucous membranes of the buccal cavity and/or the oropharynx, wherein the hydroalcoholic solution comprises between 10 and 70% ethanol and between 30 and 90% by mass of water, wherein the degree of ethanol of the hydroalcoholic solution is between 25° and 55°, and wherein said galenical form comprises between 25 and 250 mg of paracetamol for hydroalcoholic solution volumes of between 0.5 ml to 2.5 ml, wherein the concentration of paracetamol is between 50 mg paracetamol/1 ml of hydroalcoholic solution and 150 mg paracetamol/1 ml of hydroalcoholic solution.

2. The method form according to claim 1, wherein the hydroalcoholic solution comprises a pH-correcting agent.

* * * * *

UNITED STATES PATENT AND TRADEMARK OFFICE
CERTIFICATE OF CORRECTION

PATENT NO. : 8,722,744 B2  Page 1 of 1
APPLICATION NO. : 12/520723
DATED : May 13, 2014
INVENTOR(S) : Perovitch et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 835 days.

Signed and Sealed this

Twenty-ninth Day of September, 2015

Michelle K. Lee
*Director of the United States Patent and Trademark Office*